(12) United States Patent
Sentoh (10) Patent No.: US 7,381,372 B2
(45) Date of Patent: Jun. 3, 2008

(54) SAMPLE SUCTION APPARATUS

(75) Inventor: Masayasu Sentoh, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 713 days.

(21) Appl. No.: 10/879,039

(22) Filed: Jun. 30, 2004

(65) Prior Publication Data

US 2005/0042142 A1 Feb. 24, 2005

Related U.S. Application Data

(62) Division of application No. 09/899,178, filed on Jul. 6, 2001, now Pat. No. 6,833,113.

(30) Foreign Application Priority Data

Jul. 6, 2000 (JP) ............................. 2000-205358

(51) Int. Cl.
*B01L 3/02* (2006.01)
(52) U.S. Cl. .................. 422/100; 422/63; 422/64; 422/65; 422/99; 422/101; 73/23.41; 73/864.87
(58) Field of Classification Search ............ 422/63–65, 422/99–101; 73/864.87, 23.41
See application file for complete search history.

(56) References Cited

U.S. PATENT DOCUMENTS

| | | | |
|---|---|---|---|
| 4,478,495 A | 10/1984 | Samek | |
| 5,043,141 A | 8/1991 | Wilson et al. | |
| 5,173,265 A | 12/1992 | Golias et al. | |
| 5,240,679 A | 8/1993 | Stettler | |
| 5,380,486 A | 1/1995 | Anami | |
| 5,567,309 A | 10/1996 | Classon et al. | |
| 6,126,903 A | 10/2000 | Preston et al. | |
| 6,168,759 B1 * | 1/2001 | Green et al. ................... 422/64 |
| 6,180,410 B1 | 1/2001 | Gerstel et al. | |
| 6,274,087 B1 | 8/2001 | Preston et al. | |
| 6,361,744 B1 | 3/2002 | Levy | |
| 6,471,069 B2 | 10/2002 | Lin et al. | |
| 2002/0066712 A1 | 6/2002 | Brockwell | |

FOREIGN PATENT DOCUMENTS

JP 7-3328 1/1995

\* cited by examiner

*Primary Examiner*—Jill Warden
*Assistant Examiner*—Jyoti Nagpaul
(74) *Attorney, Agent, or Firm*—Birch, Stewart, Kolasch & Birch, LLP (57) ABSTRACT

A sample suction apparatus includes: first through third members; a drive source; and a suction needle provided on the third member. The drive source reduces a distance between the first member and the third member to perform: a first action of shifting the first member toward the third member to contact the first member with a portion of a specimen vessel; a second action of shifting the second member together with the third member toward the first member to contact the second member with another portion of the specimen vessel so that the specimen vessel is sandwiched between the first and second members; and a third action of shifting the third member toward the first member to bring the third member close to the second member so that the suction needle is inserted in the specimen vessel.

18 Claims, 6 Drawing Sheets

SAMPLE SUCTION APPARATUS

CROSS-REFERENCE TO RELATED APPLICATION

This application is a divisional of application Ser. No. 09/899,178, filed Jul. 6, 2001, now U.S. Pat. No. 6,833,113, which is based upon Japanese application No. 2000-205358 filed on Jul. 6, 2000, whose priority is claimed under 35 USC §119, the disclosure of which is incorporated by reference in its entirety.

BACKGROUND OF THE INVENTION

1. Field of the Invention

The present invention relates to a sample suction apparatus. In particular it relates to a so-called piercing apparatus for piercing a plug-sealed specimen vessel with a suction needle (piercer) to suck up a sample.

2. Description of Related Art

To suck up a sample such as blood out of a sealed specimen vessel, commonly employed is a method of sucking up the sample by fixing the specimen vessel and then piercing a plug of the specimen vessel with a suction needle in the shape of an injection needle. Specifically, with respect to the specimen vessel tilted to have its plug lower than its bottom, a vessel supporting means is shifted to abut the bottom of the vessel and then a washing bath for washing the suction needle is shifted to abut the plug to fix the specimen vessel. Then the suction needle penetrates the washing bath and pierces the plug to suck up the sample contained in the vessel (see Japanese Examined Utility Model Publication No. HEI 7(1995)-3328).

In a conventional apparatus as described above, two drive sources (air cylinders) are utilized to independently move the vessel supporting means, the washing bath and the suction needle. If the number of the drive source is reduced, size and production costs of the apparatus are reduced and the control thereof is simplified.

SUMMARY OF THE INVENTION

Under such circumferences, the present invention has been achieved to provide an apparatus capable of surely fixing the specimen vessel by sandwiching it at both ends and piercing the plug with the suction needle, utilizing a single drive source.

The present invention provides a sample suction apparatus comprising: a first member, a second member, and a third member capable of linearly reciprocating along the same direction and spaced apart from each other, the second member being located between the first member and the third member; a drive source provided on the third member to enlarge and reduce a distance between the first member and the third member; an elastically compressible spacer inserted between the second member and the third member; and a suction needle provided on the third member, the suction needle pointing to the first member, wherein the drive source reduces the distance between the first member and the third member to perform: a first action of shifting the first member toward the third member to contact the first member with a portion of a specimen vessel; a second action of shifting the second member together with the third member toward the first member to contact the second member with another portion of the specimen vessel so that the specimen vessel is sandwiched between the first and second members; and a third action of shifting the third member toward the first member to compress the spacer to bring the third member close to the second member so that the suction needle is inserted in the specimen vessel.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The first, second, and third members according to the present invention may be sliders mounted on a linear rail. For example, commercially available RSR-ZM type sliders manufactured by THK Co., Ltd. may be utilized. In this case, a single rail, or two or three parallel rails may be used.

It is suitable that the drive source according to the present invention reciprocates linearly. As such a drive source, fluid pressure cylinder (e.g., an air cylinder and a hydraulic cylinder), an electric cylinder driven by a motor and the like.

The elastically compressible spacer inserted between the second and third members may be, for example, a compressible spring.

In the context of the present invention, the specimen vessel is a common vessel utilized for containing samples such as blood, urea and the like. It may be a tube-shaped vessel made of glass or plastic having a bottle and an aperture sealed with a rubber plug. For example, the specimen vessel contains blood as a specimen.

The suction needle is preferably in the shape of an injection needle so that it pierces and penetrates the plug of the specimen vessel.

To perform the first action according to the present invention, the first member is independently shifted to contact an end of the specimen vessel and then the second and third members are shifted after the first member has contacted the end.

This is carried out by utilizing a stopper as the first member and a biasing member for biasing the third member toward a direction opposite to the first member. The biasing member may be a compressible spring.

The second action according to the present invention is performed in such a manner that the third member pushes the second member toward the first member via the spacer after the first member has contacted the specimen vessel and stopped.

The third action is performed in such a manner that the third member compresses the spacer after the second member has contacted the specimen vessel and stopped.

According to the present invention, the second member may be provided with a washing bath for washing the suction needle so that the suction needle is washed before or after the insertion to the specimen vessel.

The apparatus of the present invention may further comprise a sensor for detecting completion of the second action. With the sensor, all the actions may be recovered from a state where the specimen vessel does not exist between the first and second members or a state where the specimen vessel is not properly introduced.

Embodiment

Hereinafter, the present invention will be detailed by way of an embodiment with reference to the drawings, but the invention is not limited thereto.

Figure 1:
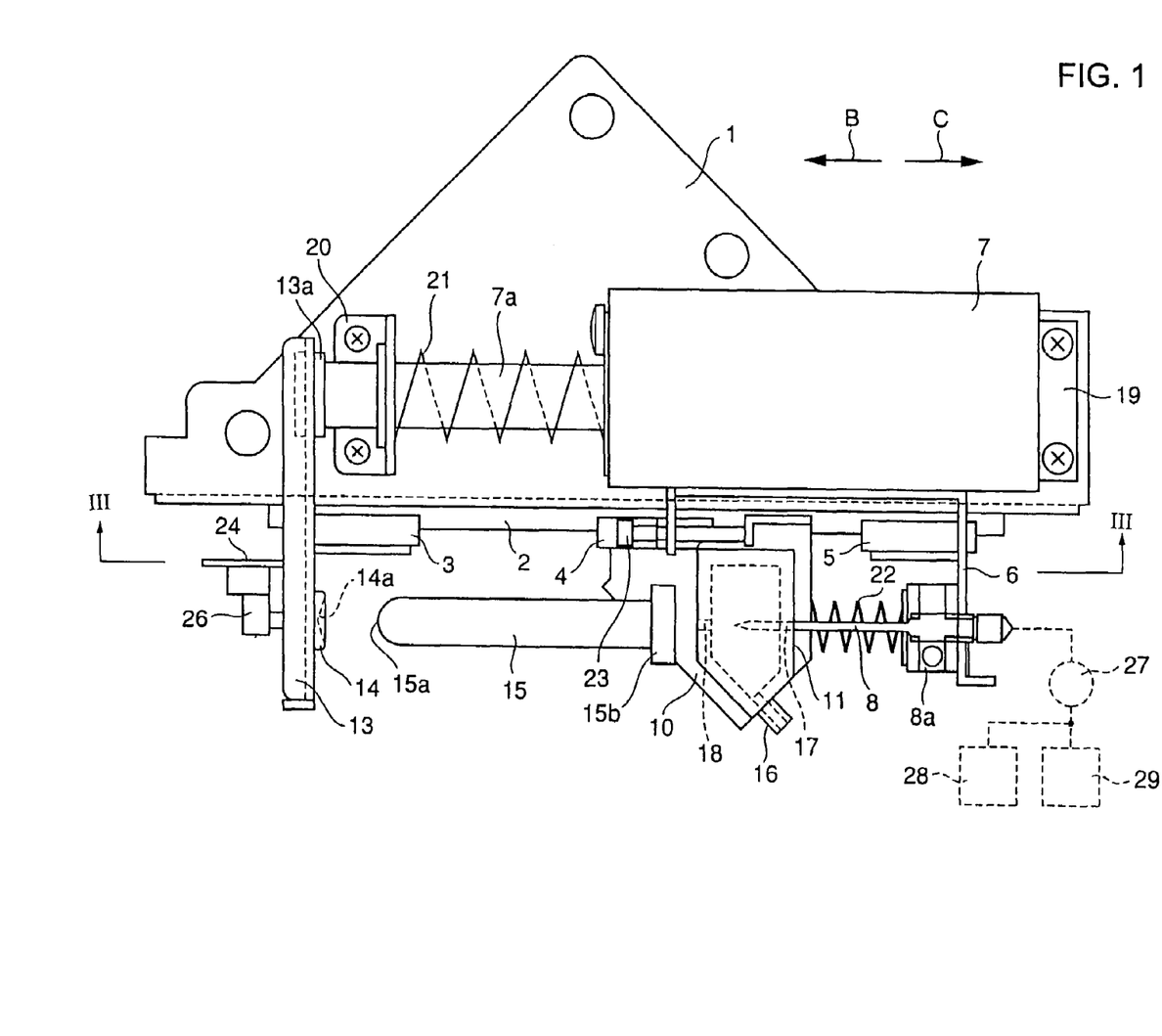
FIG. 1 is a front view for illustrating an apparatus according to an embodiment of the present invention.
Figure 2:
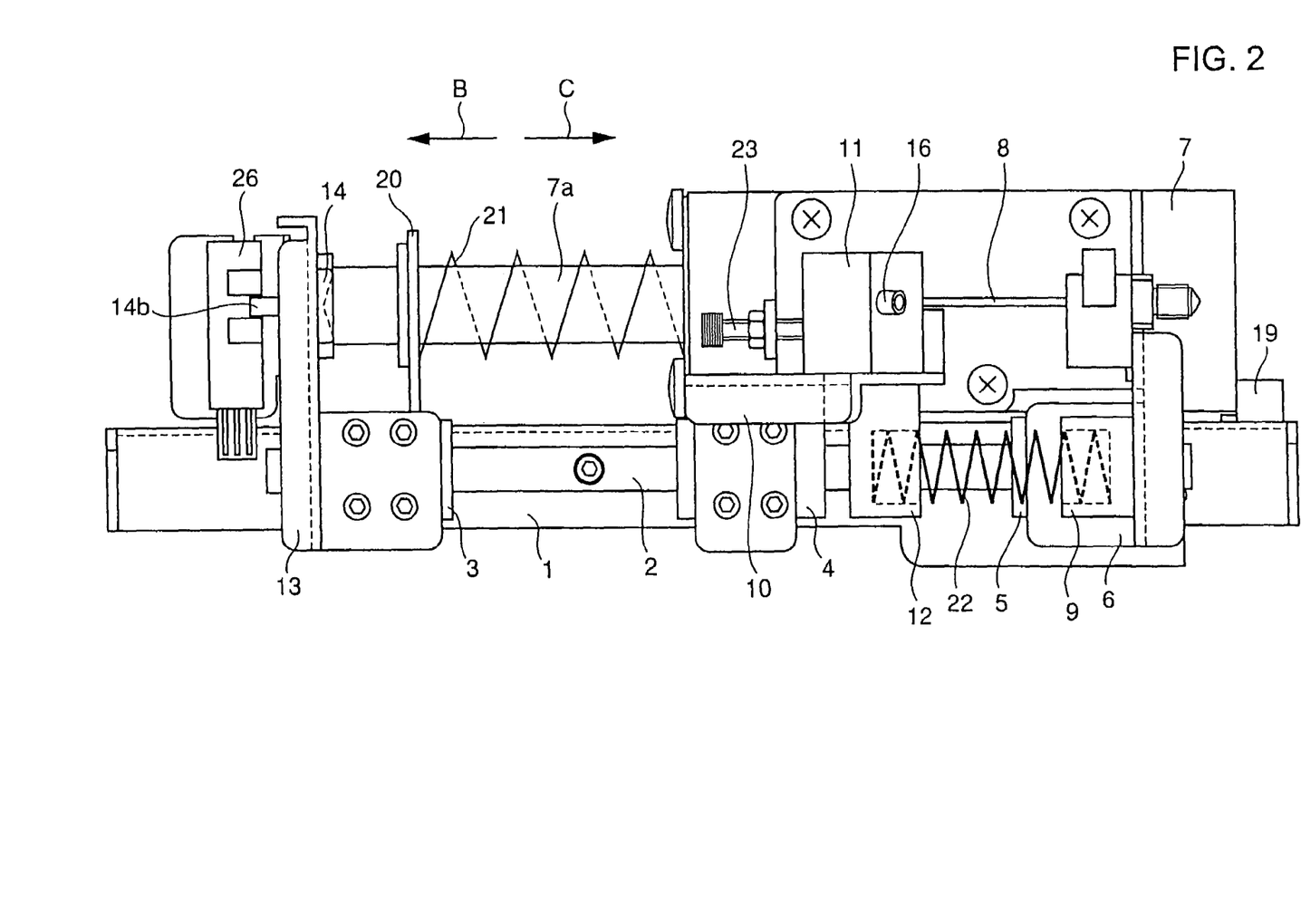
FIG. 2 is a bottom view for illustrating the apparatus according to the embodiment of the present invention.
Figure 3:
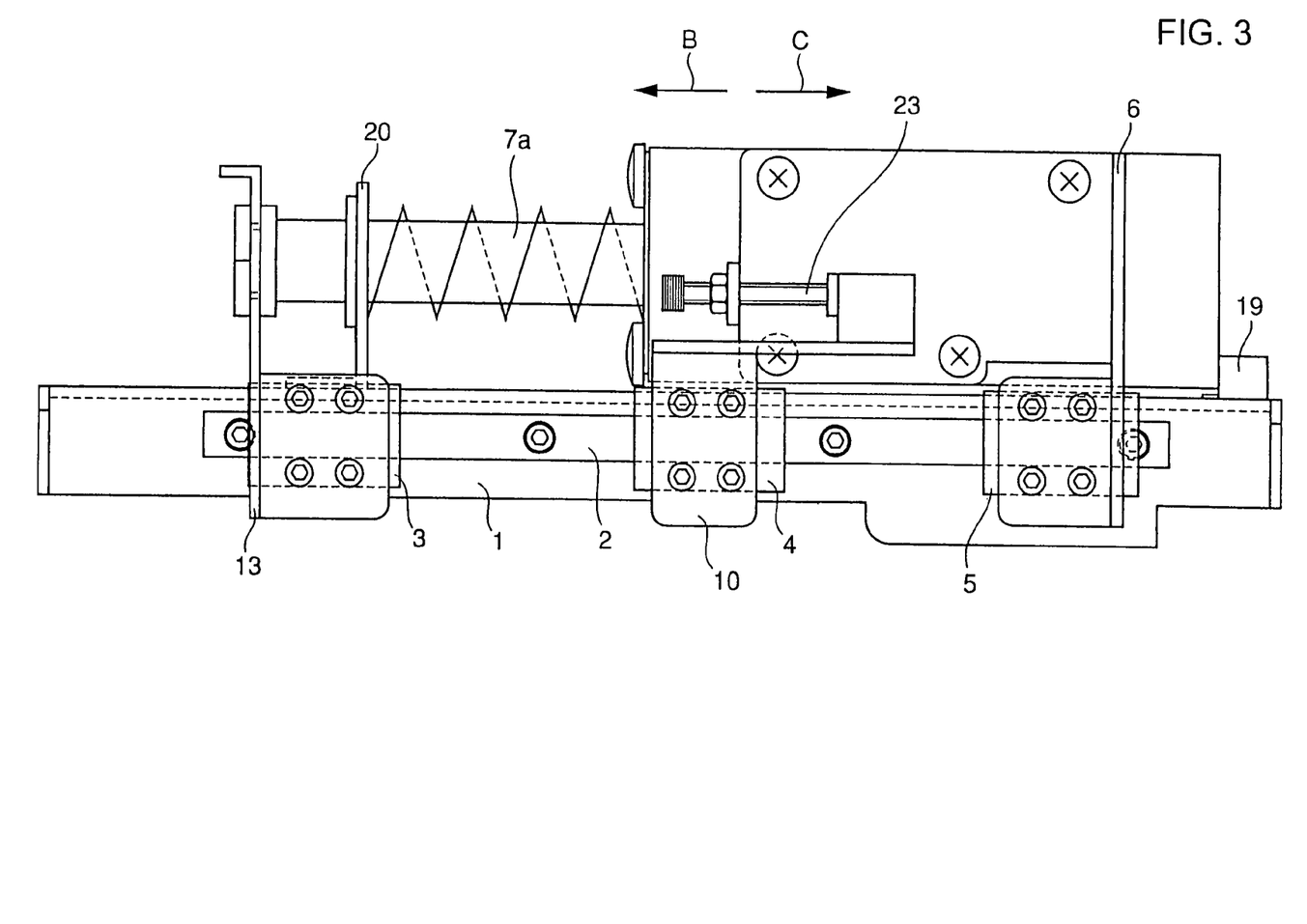
FIG. 3 is a sectional view cut along a line III-III shown in FIG. 1.

FIG. 1 is a front view for illustrating a sample suction apparatus according to an embodiment of the present invention; FIG. 2 is a bottom view for illustrating the same and FIG. 3 is a sectional view cut along a line III-III shown in FIG. 1.

As shown in these figures, a single rail 2 is fitted to a flap portion provided in a lower part of a substrate 1. Sliders 3, 4, and 5 are slidably mounted on the rail 2, which are capable of linearly reciprocating along the rail 2, respectively. On the slider 5, an air cylinder 7, a suction needle (hereinafter referred to as a piercer) 8, and a spring supporting part 9 are mounted via a mounting part 6.

On the slider 4, a washing bath 11 and a spring supporting part 12 are mounted via a mounting part 10. On the slider 3, a supporting part 14 is mounted via a mounting part 13. The mounting part 13 is connected with a distal end of a piston rod 7a of the air cylinder 7 via a connection part 13a.

The piercer 8 is mounted on the mounting part 6 via a piercer supporting part 8a. The supporting part 14 includes a conical hollow 14a to abut on a bottom 15a of a specimen vessel 15. The specimen vessel 15 contains a liquid sample such as blood to be measured and is sealed with a rubber plug 15b.

The washing bath 11 is a hollow box having a drain 16 at the bottom thereof and small pores 17 and 18 through which the piercer 8 penetrates. Stoppers 19 and 20 are mounted on the substrate 1. The stopper 19 restricts the movement of the air cylinder 7 along the direction of an arrow C shown in FIG. 1. The stopper 20 allows the piston rod 7a penetrate therethrough and restricts the movement of the connection part 13a, i.e., the mounting part 13, along the direction of the arrow C. A compressible spring 21 is wound about the piston rod 7a between the stopper 20 and the air cylinder 7 for biasing the air cylinder toward the direction of the arrow C.

Further, as shown in FIG. 2, a compressible spring 22 is supported by spring supporting parts 9 and 12 and biases the spring supporting parts 9 and 12 to keep them apart from each other. An adjusting screw 23 (FIGS. 1 and 3) is provided on the mounting part 6 so that a tip of the adjusting screw 23 abuts on the mounting part 10 to adjust a positional relationship between a tip of the piercer 8 and the washing bath 11 (during washing of the piercer 8).

Figure 4:
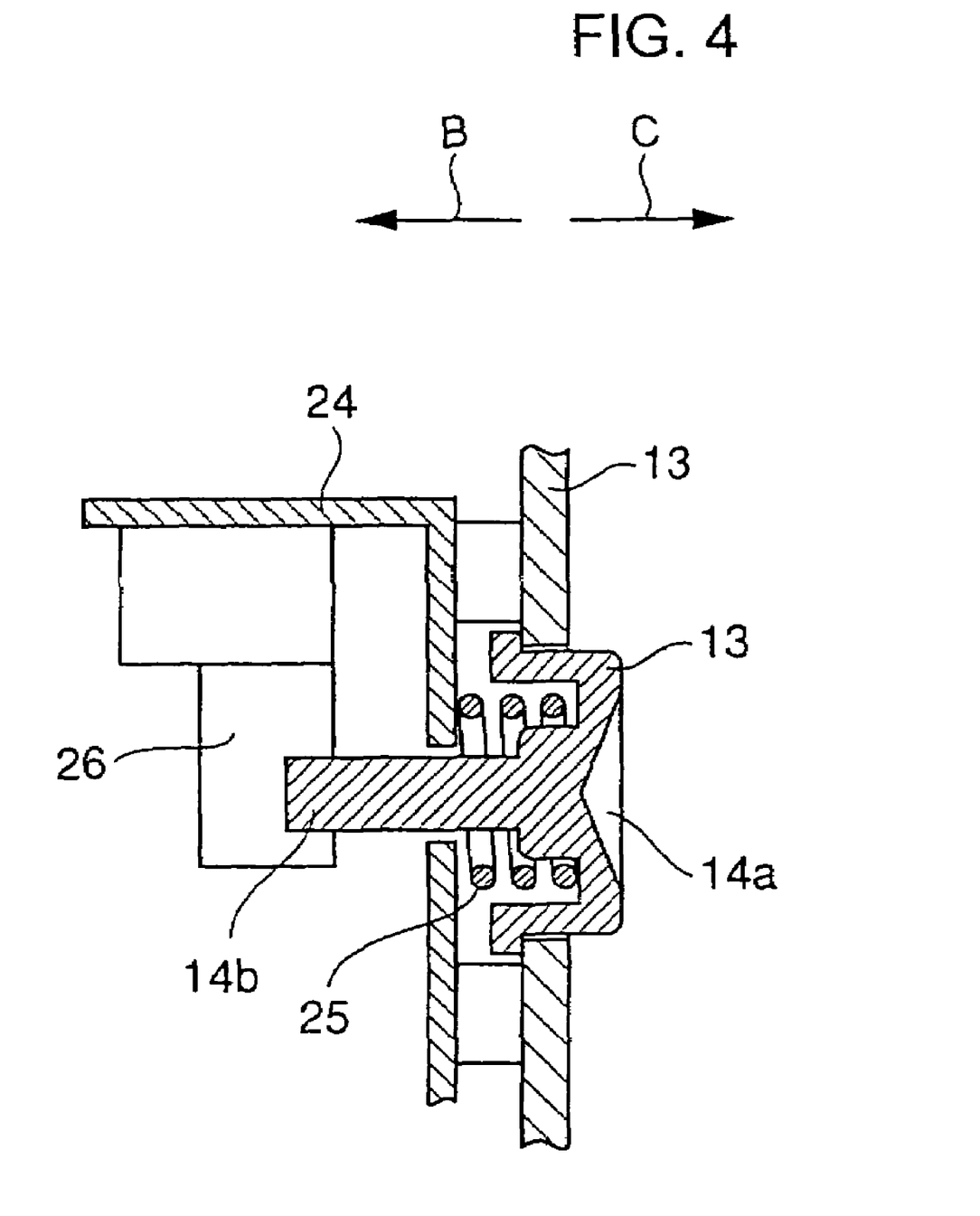
FIG. 4 is an enlarged sectional view illustrating a major part of FIG. 1.

The supporting part 14 is mounted on the mounting part 13 via a mounting plate 24 and biased toward the direction of the arrow C by a compressible spring 25 installed therein as shown in FIG. 4. Further, a photointerrupter 26 is mounted on the mounting plate 24. The photointerrupter 26 is actuated by a tip 14b of the supporting part 14 when the supporting part 14 moves along the direction of an arrow B.

The relationship in spring coefficient between the compressible springs 21, 22, and 25 is established as follows:

Compressible spring 22>compressible spring 25
Compressible spring 22>compressible spring 21

An operation procedure of the thus constructed apparatus will be detailed with reference to FIGS. 5(a) to 5(d).

Figure 5:
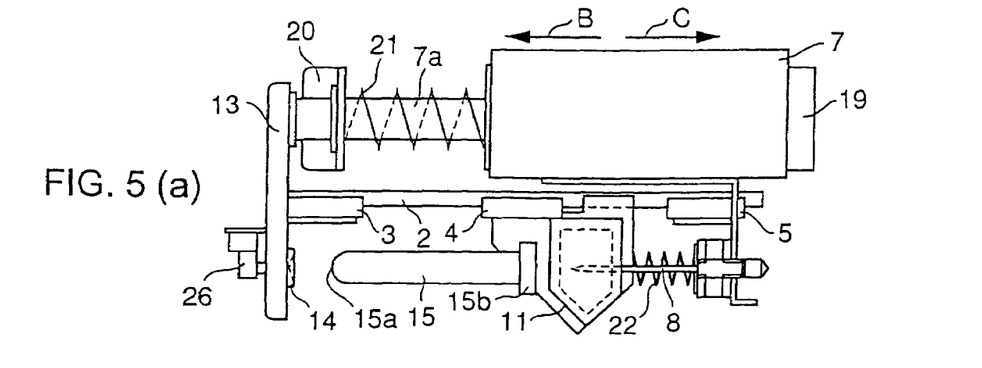
FIGS. 5(a) to 5(d) are views for illustrating an operation procedure of the apparatus according to the embodiment of the present invention.

As shown in FIG. 5(a), a specimen vessel 15 held by a hand clipper (not shown) is introduced between the supporting part 14 and the washing bath 11 of the sample suction apparatus which is in a starting state.

Then, the air cylinder 7 is actuated to drag the piston rod 7a along the direction of the arrow C. Since the compressible spring 21 is provided between the stopper 20 and the air cylinder 7 for biasing them to keep away from each other, the air cylinder 7 keeps contact with the stopper 19 without moving and the mounting part 13 is shifted along the direction of the arrow C to abut on the stopper 20 as shown in FIG. 5(b). Thus, the supporting part 14 contacts the bottom 15a of the specimen vessel 15.

As the air cylinder 7 further drags the piston rod 7a along the direction of the arrow C, the compressible spring 21 is compressed since the distal end of the piston rod 7a is fixed with the stopper 20, and then the air cylinder 7 and the mounting part 6 are shifted along the direction of the arrow B as shown in FIG. 5(c).

Simultaneously with the above, the mounting part 10 is shifted along the direction of the arrow B by force applied toward the arrow B via the compressible spring 22. Accordingly, the washing bath 11 presses the rubber plug 15b of the specimen vessel 15 in the direction of the arrow B. Thus, the specimen vessel 15 is sandwiched between the supporting part 14 and the washing bath 11, and at the same time, the supporting part 14 compresses the compressible spring 25 (FIG. 4) and the tip 14b thereof actuates the photointerrupter 26.

Then, as the air cylinder 7 further drags the piston rod 7a along the direction of the arrow C, the air cylinder 7 and the mounting part 6 are shifted toward the direction of the arrow B as shown in FIG. 5(d). At this stage, the washing bath 11 is abutting on the specimen vessel 15 and does not move, so that the compressible spring 22 is compressed and the tip of the piercer 8 passes through the small pore 18 and penetrates the rubber plug 15b to enter the specimen vessel 15.

Then, as shown in FIG. 1, a suction apparatus 28 connected with the piercer 8 is actuated to suck up the sample from the specimen vessel 15 via the piercer 8. A predetermined amount of the sucked sample is collected by a quantitative measurement part 27.

After the suction of the sample has been completed, the air cylinder 7 pushes out the piston rod toward the direction of the arrow B. As a result, the actions carried out in the order of FIGS. 5(a) to 5(d) are performed in an opposite order. When the sample suction apparatus returns to the state shown in FIG. 5(a), washing solution is supplied from a washing apparatus 29 (FIG. 1) to the washing bath 11 via the piercer 8.

The washing solution is also supplied toward the piercer 8 from a cap (not shown) formed in the washing bath 11 so that the inner and outer walls of the piercer 8 are washed. Waste solution is then discharged from the drain 16.

Thus, the suction of the sample via the piercer 8 and the washing of the piercer 8 are performed.

In the case where the photointerrupter 26 is not actuated while shifting from the state of FIG. 5(b) to the state of FIG.

5(c), a control section (not shown) judges that the specimen vessel 15 is absent or introduced improperly between the supporting part 14 and the washing bath 11, and then returns the sample suction apparatus to the state of FIG. 5(a).

For easy suction of the sample from the specimen vessel 15 via the piercer 8, it is preferable to incline the specimen vessel 15 by 30 to 45° with respect to a horizontal line so that the bottom 15a is held higher than the rubber plug 15b. The inclination is carried out by adjusting the degree of angle of the substrate 1 with respect to the horizontal line. In this case, the rail 2 is also inclined and thus the air cylinder 7 is always biased toward the stopper 19 by its weight, so that the compressible spring 21 is omitted.

Figure 6:
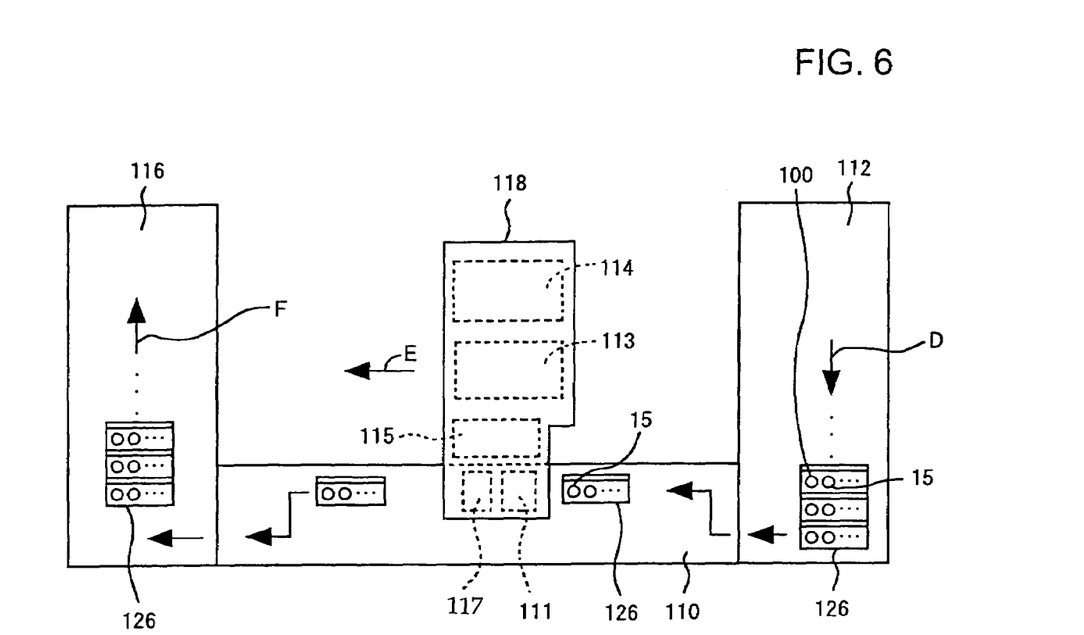
FIG. 6 is a plan view for illustrating an arrangement of a hematology analyzer utilizing the sample suction apparatus shown in FIG. 1.

FIG. 6 is a view for illustrating an arrangement of a hematology analyzer provided with the sample suction apparatus of the present invention.

Racks 126 each have the shape of a test tube stand capable of carrying ten specimen vessels 15.

The racks 126 each carrying the specimen vessels 15 are arranged along a vertical line on a conveyer 112. Then, all the racks 126 move toward a direction of an arrow D indicated in FIG. 6 and the rack 126 at the front is transferred to a conveyer 110 located on the left hand of the conveyer 112.

A hematology analyzer 118 is provided above the conveyer 110. The rack 126 transferred on the conveyer 110 is stopped immediately below a stirrer 111 of the hematology analyzer 118.

After a specimen in one of the specimen vessels 15 at the front is stirred with the stirrer 111, the rack 126 moves by a predetermined distance (an arrangement pitch among the specimen vessels 15 on the rack 126). The specimen vessel 15 immediately after subjected to stirring is held by a hand clipper 117 and withdrawn from the rack 126 to suck up the specimen (blood) by a suction apparatus 115, and then returned to the rack 126. The sucked specimen is quantified by a quantitative measurement part 113 and analyzed by an analysis part 114. While the suction apparatus 115 sucks up the specimen from the preceding specimen vessel, the stirrer 111 stirs a specimen contained in the next specimen vessel 15.

Thus, the rack 126 moves intermittently by the arrangement pitch of the specimen vessels 15. After the stirring and the suction of the specimen in the ten specimen vessels 15 (all the specimen vessels carried on the rack 126) are completed, the rack 126 is transferred along a direction of an arrow E. Then the specimen vessel 15 at the front of the following rack 126 is subjected to stirring. The racks 126 that went through the stirring and the suction of the specimen in the ten specimen vessels are finally collected at a rack collecting part 116 and arranged along a direction of an arrow F.

In the hematology analyzer 118, the sample suction apparatus shown in FIG. 1 is utilized as the suction apparatus 115.

According to the present invention, the action of fixing the specimen vessel and the action of inserting the suction needle in the specimen vessel are performed with a single drive source, so that the structure and the control of the sample suction apparatus are simplified.

What is claimed is:

1. A sample suction apparatus for aspirating a specimen from a specimen vessel by using a suction needle, comprising:
    a drive source;
    a first movable member supporting a first end of the specimen vessel and operable to be movable by the drive source;
    a second movable member supporting a second end of the specimen vessel and operable to be movable by the drive source; and
    a third movable member holding the suction needle and operable to be movable by the drive source,
    wherein the second movable member is arranged between the first movable member and the third movable member and
    wherein a spacer comprising a resilient member is arranged between the second and third movable members, the spacer maintaining a distance between the second and third movable members.

2. A sample suction apparatus according to claim 1, wherein the specimen vessel is sandwiched between the first movable member and the second movable member so that the suction needle is inserted into the specimen vessel.

3. A sample suction apparatus according to claim 1, wherein the resilient member is a compressible spring.

4. A sample suction apparatus according to claim 1, further comprising:
    a sensor for detecting whether the specimen vessel is present or not between the first and second movable members.

5. A sample suction apparatus according to claim 1, wherein the first movable member includes a sensor for detecting contact of the specimen vessel.

6. A sample suction apparatus according to claim 1, wherein the specimen vessel contains blood as the specimen.

7. A sample suction apparatus for aspirating a specimen from a specimen vessel by using a suction needle, comprising:
    a drive source;
    a first movable member supporting a first end of the specimen vessel and operable to be movable by the drive source;
    a second movable member supporting a second end of the specimen vessel and operable to be movable by the drive source;
    a third movable member holding the suction needle and operable to be movable by the drive source;and:
    a rail,
    wherein the first, second, and third movable members are slidably mounted on the rail and
    wherein the second movable member is arranged between the first movable member and the third movable member.

8. A sample suction apparatus according to claim 7, wherein the first, second and third movable members are capable of linearly moving along the rail.

9. A sample suction apparatus according to claim 7, further comprising:
    a substrate holding the rail.

10. A sample suction apparatus according to claim 9, wherein the substrate holds a stopper for restricting movement of the first movable member toward the third movable member.

11. A sample suction apparatus according to claim 10, further comprising:
    a biasing member for biasing the third movable member toward a direction opposite to the first movable member.

12. A sample suction apparatus for aspirating a specimen from a specimen vessel by using a suction needle, comprising:
    a drive source:
    a first movable member supporting a first end of the specimen vessel and operable to be movable by the drive source;

a second movable member supporting a second end of the specimen vessel and operable to be movable by the drive source; and a third movable member holding the suction needle and operable to be movable by the drive source, wherein the second movable member is arranged between the first movable member and the third movable member and wherein the drive source includes an air cylinder having a piston rod, the air cylinder being provided on the third movable member and a distal end of the piston rod being connected with the first movable member.

13. A sample suction apparatus according to claim 12, further comprising:

a spacer arranged between the second and third movable members, the spacer maintaining a distance between the second and third movable members.

14. A sample suction apparatus according to claim 13, wherein the spacer is a resilient member.

15. A sample suction apparatus according to claim 14, wherein the resilient member is a compressible spring.

16. A sample suction apparatus according to claim 12, further comprising:

a first spacer arranged between the second and third movable members, the first spacer maintaining a distance between the second and third movable members; and a second spacer is attached to the piston rod.

17. A sample suction apparatus according to claim 12, further comprising:

a first spring arranged between the second and third movable members, the first spring maintaining a distance between the second and third movable members; and a second spring is attached to the piston rod;

wherein the second spring has a spring coefficient smaller than a spring coefficient of the first spring.

18. A sample suction apparatus for aspirating a specimen from a specimen vessel by using a suction needle, comprising:

a drive source:

a first movable member supporting a first end of the specimen vessel and operable to be movable by the drive source:

a second movable member supporting a second end of the specimen vessel and operable to be movable by the drive source, wherein the movable second member includes a washing bath for washing the suction needle;

a third movable member holding the suction needle and operable to be movable b the drive source, wherein the second movable member is arranged between the first movable member and the third movable member.

* * * * *